United States Patent [19]

Cole

[11] Patent Number: 5,312,345
[45] Date of Patent: May 17, 1994

[54] ANTI-NEEDLE STICK PROTECTIVE INNER BLUNT TUBULAR STYLET FOR INTRAVENOUS THERAPY

[76] Inventor: Richard D. Cole, 311 Oleander Dr., San Jacinto, Calif. 92582

[21] Appl. No.: 848,878

[22] Filed: Mar. 11, 1992

[51] Int. Cl.$^5$ .............................................. A61M 5/00
[52] U.S. Cl. .................... 604/110; 604/164; 604/267
[58] Field of Search ............... 604/267, 164, 165, 168, 604/170, 239, 158, 110, 165, 162, 168, 158–159, 264, 280

[56] References Cited

U.S. PATENT DOCUMENTS

| | | | |
|---|---|---|---|
| 3,262,448 | 7/1966 | Ring et al. | 604/159 |
| 3,438,373 | 4/1969 | Pannier, Jr. | 604/159 |
| 3,463,152 | 8/1969 | Sorenson | 604/162 |

FOREIGN PATENT DOCUMENTS 0331318  9/1989  European Pat. Off. ............ 604/280

*Primary Examiner*—John D. Yasko
*Assistant Examiner*—Vanitha Alexander

[57] ABSTRACT

The invention is a new and unique device much needed to protect the health care providers from the leading cause of exposure to blood born diseases in their profession, this being inadvertent needle sticks by contaminated needles. Dirty needle stick accidents are one of the major means in which health care providers are exposed to the HIV virus on the job. The invention is a blunt tubular stylet that is inserted into the commonly used intravenous therapy device. Initially it is positioned inside the needle stylet in a retracted position, by means of the friction catches. This allows the cutting tip of the existing intravenous therapy device's cutting tip to be exposed. Upon successful venipuncture the invention is positioned so its blunt tubular stylet is advanced beyond the intravenous therapy venipuncture device's cutting tip, obscuring it. Upon withdrawal of the intravenous therapy venipuncture device, the sharp cutting tip of its needle stylet is fully protected by the invention's blunt metal stylet. The intravenous therapy device's needle stylet along with the inventions blunt tubular stylet firmly secured within now can be safely disposed of.

1 Claim, 1 Drawing Sheet

ANTI-NEEDLE STICK PROTECTIVE INNER BLUNT TUBULAR STYLET FOR INTRAVENOUS THERAPY

BACKGROUND OF THE INVENTION

A small blunt metal tubular stylet with a hard plastic hub, which comes in various sizes and lengths to fit inside various sized intravenous therapy catheter-over-needle devices.

This tubular stylet is designed to fit inside the needle stylet of existing commonly used intravenous therapy venipuncture devices. In the retracted position the tubular stylet allows the cutting edge of the needle stylet to be exposed to allow venipuncture.

Upon successful venipuncture with a commonly used venipuncture device the blunt tubular stylet is designed to be advanced forward, protruding beyond the needle stylet's cutting edge, obscuring the sharp cutting tip of the needle stylet. The blunt tubular stylet is firmly secured in place within the needle stylet by friction ridges or metal catches designed into the periphery of the hard clear plastic hub which is attached to one of the ends of the blunt tubular stylet.

The stylet being a hollow tube will allow the blood to capillary back into the clear hard plastic hub on the opposite end of the blunt tubular stylet. This will allow the intravenous therapist to observe for the blood flashback, which will indicate to the therapist that a successful venous access has been achieved. The purpose of the blunt tubular stylet is to protrude beyond the needle stylets of existing commonly used venipuncture devices obscuring its sharp cutting edges. This is done after achieving a successful venipuncture. Upon withdrawal of the needle stylet this will prevent accidental needle sticks from blood contaminated needles. This will result in a great reduction in the spread of blood born disease to patients and health care providers.

SUMMARY OF THE INVENTION

This is a sander metal tube designed to fit within the inner bore of the needle stylet of existing commonly used catheter-over-needle or needle type intravenous therapy devices for the purpose to form a protruding blunt protective stylet.

On one end of the stylet is a clear hard plastic hub with friction ridges or barbs to facilitate a snug secure fit of the blunt tubular stylet into the needle stylet when advanced. The plastic hub is also shaped to allow fitting of any existing commonly used medical syringe tip or intravenous therapy tubing's male connection by means of friction fit or Luer lock fit.

DESCRIPTION OF THE PREFERRED EMBODIMENTS

Figure 1:
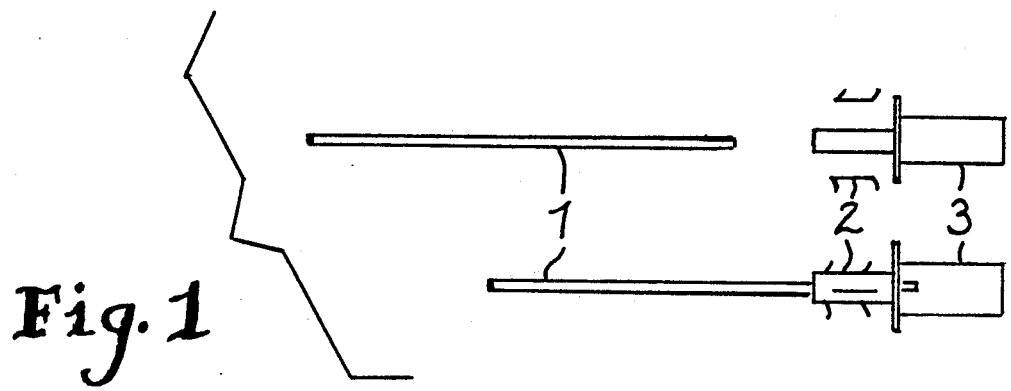
FIG. 1.—Sideview of the blunt tubular stylet device.

The blunt tubular stylet in its entirety is shown in FIG. 1. Stylet (1) and friction catches (2) are firmly and permanently affixed to hub (3).

Figure 3:
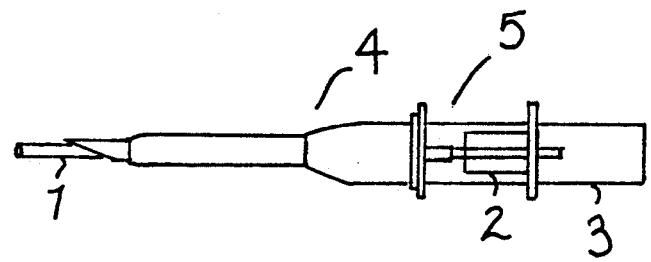
FIG. 3.—Sideview showing the blunt tubular stylet device inserted and fully advanced in the protective position, within a conventional intravenous therapy catheter-over-needle venous access device.

A hollow metal stylet (1) which is blunt at both ends and that come in various lengths and diameters to accommodate the spectrum of sizes that are available with commonly used intravenous therapy devices today. Stylet (1) is bonded permanently to hub (3). Small barbed projections (2) bonded permanently into hub (3). Barbed projections (2) are designed as friction catches to secure the device(s) securely into the intravenous therapy venipuncture device (4) as seen in FIG. 3. Stylet (1) and barbed projections (2) are permanently affixed to the clear hard plastic hub (3). Stylet (1) is affixed on one end of hub (3), in a manner to form a free unobstructed channel from the exposed end of the blunt tubular stylet to the end enclosed within the clear hard plastic hub. The clear plastic hub is shaped and sized to fit securely into existing intravenous therapy vascular access device's needle stylet's hub. The opposite end of the clear hard plastic hub is shaped and sized to accommodate the fitting of existing conventional medical syringe tips and the male connector end of the intravenous therapy tubing by means of a friction or Luer lock connection.

Figure 2:
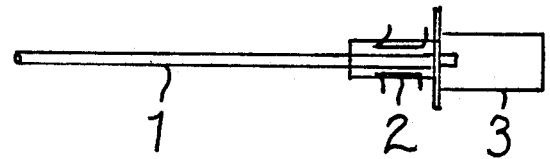
FIG. 2.—Cross-section view to the blunt tubular stylet device.

A cross section view of the blunt tubular stylet is shown in FIG. 2. Stylet (1) is the hollow metal blunt stylet. Barbed projections (2) are the barbed friction catches. Hub (3) is the clear hard plastic hub.

The entire blunt stylet device as it is seen when it is inserted into the intravenous therapy catheter-overneedle venipuncture device is shown in FIG. 3. FIG. 3 shows the blunt metal stylet in its fully advanced position. The blunt stylet in this advanced safety position extends beyond the needle stylet's cutting tip, obscuring it.

I claim:
1. A safety device used to prevent accidental needle sticks upon withdrawal of sharp intravenous puncture devices comprising:
  (a) a hollow tubular stylet with two blunt ends of which first end protrudes beyond a tip of said sharp intravenous puncture device, such as a needle stylet, to obscure said tip when inserted into said intravenous puncture device,
  (b) a clear plastic cylindrical hub to which said hollow tubular stylet is permanently bonded on second end and is designed to allow easy and secure fitting to all conventional sized medical syringes tips and male connectors of existing commonly used intravenous therapy tubing by either friction fit of Luer lock connection and
  (c) barbed friction catches which are molded on said hub to form a permanent component of said hub and secures the safety device within the intravenous puncture device.

* * * * *